United States Patent
Annis

[11] Patent Number: 5,510,505
[45] Date of Patent: Apr. 23, 1996

[54] ARTHOPODICIDAL OXADIAZINE INTERMEDIATE

[75] Inventor: Gary D. Annis, Landenberg, Pa.

[73] Assignee: E. I. Du Pont de Nemours and Company, Wilmington, Del.

[21] Appl. No.: 418,047

[22] Filed: Apr. 6, 1995

[51] Int. Cl.$^6$ .................................................. C07C 261/00
[52] U.S. Cl. .................................................................. 560/28
[58] Field of Search .................................. 560/28; 544/66

[56]  References Cited

FOREIGN PATENT DOCUMENTS

WO92/12249  7/1992  WIPO .......................... C07D 273/04
WO93/19045  9/1993  WIPO .......................... C07D 207/20

Primary Examiner—Paul F. Shaver
Assistant Examiner—Joseph M. Conrad, III

[57] ABSTRACT

Provided is a compound of the formula:

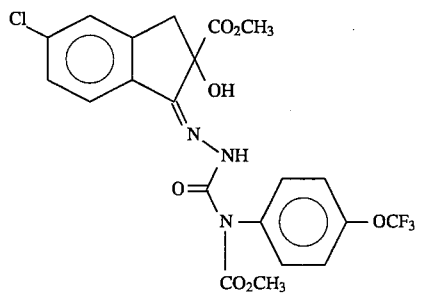

This compound is an intermediate to and is used for preparing the arthropodicidal oxidiazine Compound II described in the specification.

1 Claim, No Drawings

ARTHOPODICIDAL OXADIAZINE INTERMEDIATE

BACKGROUND OF THE INVENTION

The present invention pertains to an intermediate for the preparation of an arthropodicide. More particularly, the present invention pertains to methyl 5-Chloro-2,3-dihydro-2-hydroxy-1-(((((N-(methoxycarbonyl)-N-((4-(trifluoromethoxy)phenyl))amino))carbonyl))hydrazono))-1H-indene-2-carboxylate (designated Compound I) which is an intermediate in the preparation of an arthropodicidal oxadiazine. Oxadiazines such as those disclosed in WO 9211249 and WO 9319045 are important arthropodicidal compounds, and effective preparative methods are needed. Compound II, depicted below, is a particularly advantageous arthropodicidal oxadiazine.

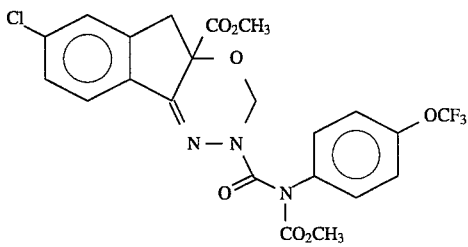

Accordingly, this invention provides Compound I which is a useful intermediate for the preparation of II. WO 9319045 describes generically methods for preparing various intermediates, including those of a type similar to Compound I.

SUMMARY OF THE INVENTION

According to the present invention there is provided Compound I which is depicted as follows.

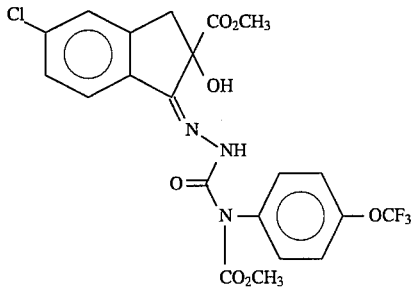

According to the present invention there is also provided a process to make Compound II from Compound I.

DETAILS OF THE INVENTION

The arthropodicidal oxadiazine Compound II can be prepared by reaction of Compound I with an acetal derivative in the presence of a Lewis acid, optionally in the presence of an acid scavenger. The acetal derivative, is a dialkoxyalkane of 3 to 12 carbon atoms, such as dimethoxymethane, diethoxymethane and the like. It is preferably present in the reaction mixture in excess and can also serve as a solvent. In addition, solvents such as chloroform, dichloroethane, dichloromethane, tetrahydrofuran and the like can be employed as a co-solvent. The Lewis acid can be boron trifluoride, phosphorous pentoxide, sulfur trioxide and the like, and is usually present in excess. Phosphorous pentoxide and sulfur trioxide are preferred. Sulfur trioxide may be used in the form of a complex, for example with dimethylformamide (viz., $SO_3.DMF$), and usually there is also present an acid scavenger such as an amine complex (e.g., $SO_3.Pyridine$). A filter aid such as Celite® (diatomaceous earth) can be added to the reactions employing phosphorus pentoxide. The reaction temperature is typically in the range of 0° to 110° C., with a temperature of about 40° to 70° C. being preferred. The reaction is usually complete within a few hours. The product can be isolated by standard methods such as quenching with aqueous base, extraction of the organics, concentration and crystallization for the sulfur trioxide reactions or alternatively filtration, washing with aqueous base, concentration and crystallization for the phosphorous pentoxide reactions.

Compound I can be prepared by reacting Compound III and Compound IV (Equation 1) in an inert solvent such as chloroform, dichloromethane, benzene, toluene, dimethoxy ethylene glycol (glyme) and the like in the presence of an acid scavenger such as triethylamine, aqueous sodium bicarbonate and the like. Reaction temperatures can be in the range of about −10° to 60° C., with about 25° C. being preferred. The reaction is usually complete within a few hours. The product is isolated by standard methods such as aqueous work up, concentration and crystallization from a suitable solvent.

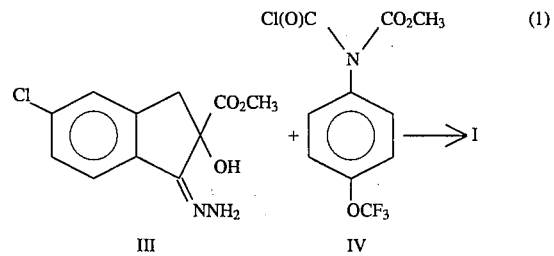

Compound III can be prepared by reacting methyl 5-chloro-2,3-dihydro-2-hydroxy- 1-oxo-1H-indene-2-carboxylate with hydrazine monohydrate according to the first part of step B of Example 2 in WO 9211249. As described therein, Compound III was isolated as a yellow solid but not named.

Compound IV can be prepared by treating Compound V (Equation 2) with base such as sodium hydride, sodium methoxide and the like in a solvent such as benzene, toluene and the like and a co-solvent such as glyme to form the corresponding salt of V, then treating this salt with an excess of phosgene. Reaction temperatures are in the range of about −10° to 100° C. with a range of 25° to 60° C. being preferred. The reaction is usually complete in a few hours.

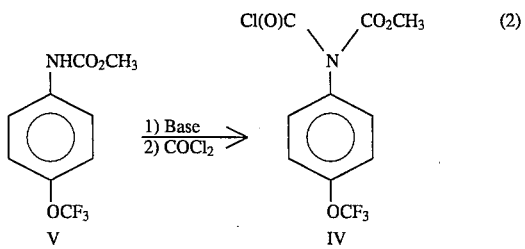

Compound V may be prepared from the compound VI by standard methods. One such method involves reacting Compound VI with methyl chloroformate in the presence of acid scavenger such as diethylaniline, triethylamine, aqueous potassium carbonate and the like (Equation 3), optionally in a solvent such as diethyl ether, dichloromethane and the like. Reaction temperatures are typically in the range of about 0° to 100° C. with temperatures 25° to 70° C. being preferred. The reaction is usually complete within a few hours.

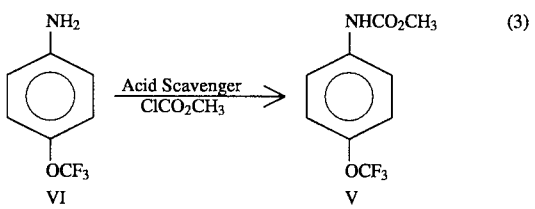

The following Examples serve to illustrate the present invention.

EXAMPLE 1

Preparation of methyl 5-chloro-2,3-dihydro-2-hydroxy-1-((((((N-(methoxycarbonyl)-N((4-(trifluoromethoxy)phenyl))amino))-carbonyl))hydrazono))-1H-indene-2-carboxylate (Compound I).

Methyl chloroformate, 5.4 g (0.0571 moles), was added to a mixture of 5 g (0.0282 moles) of p-trifluoromethoxyaniline and 10.5 g (0.0704 moles) of N,N-diethylaniline cooled in an ice bath. When the addition was complete, the mixture was warmed to 70° C. then allowed to cool to ambient temperature and poured into 200 mL of 1N hydrochloric acid. This mixture was extracted with three 50 mL aliquots of ethyl acetate, and the combined extracts were washed with 100 mL of 1N hydrochloric acid, dried with $MgSO_4$, and evaporated to give 5 g of Compound V.

$^1$H NMR ($CDCl_3$, 400 MHz) δ7.41 (d, 2H), 7.16 (d, 2H), 6.67 (s, 1H), 3.78 (s, 3H).

Compound V, 4 g (0.0170 moles), was added to 0.68 g (0.0.170 moles) of sodium hydride, 40 mL of benzene, and 8 mL of 1,2-dimethoxyethane and the mixture was gently warmed until gas evolution ceased. The mixture was allowed to cool to ambient temperature and then diluted with benzene until the mixture, a slurry, was thin enough to transfer. The slurry, was added to 60 mL of a 1.93M solution of phosgene in toluene at 0° to 10° C. After the addition, the mixture was allowed to warm to room temperature and excess phosgene was removed by the passing nitrogen gas through the mixture, whereupon the volume of the mixture was reduced by about half. Compound IV was present in solution and was reacted, without isolation, in the next step.

The above mixture containing IV was added to a mixture of 4.33 g (0.0170 mol) of methyl 5-chloro-1-hydrazono-2,3-dihydro-2-1H-indene-2-carboxylate (Compound III) and 1.68 g (0.0166M) of triethylamine in 50 mL of dichloromethane. The combined mixture was stirred at ambient temperature for 2 h. This mixture was then poured into 1 L (1N) hydrochloric acid and extracted with three 500 mL aliquots of ethyl acetate. The combined extracts were dried with $MgSO_4$ and concentrated to effect crystallization of the product from solution. The crystals were collected, washed with ether/hexanes and dried to give 5.22 g of Compound I, m.p. 168°–168.5° C.

IR (nujol) 3394, 3228, 1753, 1738, 1681, 1641, 1594, 1546, 1524, 1503, 1421, 1327, 1241, 1179, 1135, 1087, 1048, 1021, 963,877, 835 cm$^{-1}$. $^1$H NMR (400 MHz, $CDCl_3$) δ12.54 (s, 1H), 7.80 (d, 1H), 7.30–7.20 (m, 6H), 4.41 (s,1H), 3.79 (s, 3H), 3.76 (s, 3H), 3.50 ( ½ABq, 1H) 3.36 (½ABq, 1H).

EXAMPLE 2

Illustration of the preparation of arthropodicidal Compound II from Compound I.

Phosphorus pentoxide, 42 g (0.295 mole), was added to a mixture of 60.71 g (0.118 moles) of compound I, 60 g of Celite®, 400 mL of dimethoxymethane, and 400 mL of dichloroethane. The mixture was refluxed for 4.5 h, then an additional portion of phosphorus pentoxide, 4.4 g (0.0309 mole) of was added and the mixture was refluxed for an additional 0.5 h. The mixture was filtered through Celite® after which the Celite® was washed thoroughly with dichloromethane. The filtrate, comprising the dichloroethane and dichloromethane solutions, was washed with 1 L of saturated sodium bicarbonate solution, filtered again and dried with magnesium sulfate. The filtrate was concentrated to a volume of 1800 mL and was washed again with 800 mL of saturated sodium bicarbonate solution. The organic layer was dried with $MgSO_4$ and concentrated to give compound II as a viscous oil which was crystallized from hexanes/diethylether to give 46 g of solid. The spectral properties of II were consistent with a compound of this structure.

What is claimed is:

1. A compound having the formula:

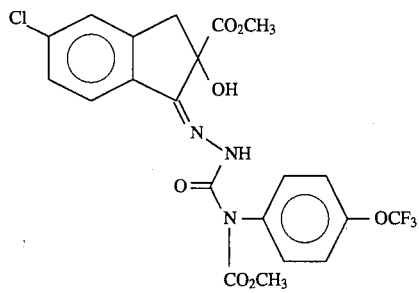

* * * * *